United States Patent [19]

Theeuwes

[11] Patent Number: 5,030,454
[45] Date of Patent: * Jul. 9, 1991

[54] METHOD FOR DELIVERING DRUG IN TINY PILLS IN LIQUID CARRIER

[75] Inventor: Felix Theeuwes, Los Altos, Calif.

[73] Assignee: Alza Corporation, Palo Alto, Calif.

[*] Notice: The portion of the term of this patent subsequent to Aug. 1, 2006 has been disclaimed.

[21] Appl. No.: 370,668

[22] Filed: Jun. 23, 1989

Related U.S. Application Data

[63] Continuation of Ser. No. 112,189, Oct. 26, 1987, Pat. No. 4,853,229.

[51] Int. Cl.5 ............................................. A61K 9/66
[52] U.S. Cl. .................................. 424/455; 424/450
[58] Field of Search ................ 424/455, 454, 459, 490

[56] References Cited

U.S. PATENT DOCUMENTS

| | | | |
|---|---|---|---|
| 2,738,303 | 3/1956 | Blythe | 424/458 |
| 2,793,979 | 5/1957 | Svedres | 424/470 |
| 2,897,121 | 7/1959 | Wagner | 428/497 |
| 2,921,883 | 1/1960 | Reese et al. | 424/458 |
| 2,951,792 | 9/1960 | Swintosky | 424/472 |
| 2,953,497 | 9/1960 | Press | 424/470 |
| 2,996,431 | 8/1961 | Barry | 424/7.1 |
| 3,080,294 | 3/1963 | Shepard | 424/498 |
| 3,081,233 | 3/1963 | Enz et al. | 424/462 |
| 3,109,775 | 11/1963 | Shepard et al. | 424/498 |
| 3,139,383 | 6/1964 | Neville | 424/462 |
| 3,185,625 | 5/1965 | Brown | 424/494 |
| 3,328,256 | 6/1967 | Gaunt | 424/501 |
| 3,390,050 | 6/1968 | Speiser | 424/97 |
| 3,432,592 | 3/1969 | Speiser | 424/468 |
| 3,492,397 | 1/1970 | Peters et al. | 424/495 |
| 3,922,379 | 11/1975 | Farhadieh | 424/491 |
| 4,044,149 | 8/1977 | Fields et al. | 424/80 |
| 4,140,755 | 2/1979 | Sheth et al. | 424/472 |
| 4,167,558 | 9/1979 | Sheth et al. | 424/465 |
| 4,176,175 | 11/1979 | Maekawa et al. | 424/480 |
| 4,178,361 | 12/1979 | Cohen et al. | 424/487 |
| 4,221,778 | 9/1980 | Raghunathan | 424/483 |
| 4,434,153 | 2/1984 | Urquhart et al. | 424/22 |
| 4,452,862 | 6/1984 | Markert et al. | 424/482 |
| 4,548,598 | 10/1985 | Theeuwes | 604/251 |
| 4,647,599 | 3/1987 | Bezzegh et al. | 423/105 |
| 4,656,028 | 4/1987 | Cuca | 424/455 |
| 4,764,380 | 8/1988 | Urquhart et al. | 424/458 |
| 4,853,229 | 8/1989 | Theeuwes | 424/455 |

FOREIGN PATENT DOCUMENTS

| | | |
|---|---|---|
| 523594 | 7/1940 | Switzerland . |
| 931532 | 11/1959 | United Kingdom . |
| 1098006 | 1/1968 | United Kingdom . |
| 8503000 | 7/1985 | World Int. Prop. O. . |
| 8707833 | 12/1987 | World Int. Prop. O. . |

Primary Examiner—Merrell C. Cashion, Jr.
Assistant Examiner—Leon R. Horne
Attorney, Agent, or Firm—Paul L. Sabatine; Edward L. Mandell; Steven F. Stone

[57] ABSTRACT

A delivery system is disclosed for delivering a beneficial agent to an environment of use. The delivery system comprises a plurality of tiny dosage forms comprising a beneficial agent. The delivery system also comprises means for maintaining (a) the physical and chemical integrity of the dosage form and for (b) inhibiting delivery of the beneficial agent during non-performance of the delivery system.

1 Claim, 5 Drawing Sheets

FIG.5
FIG.6
FIG.7
FIG.8
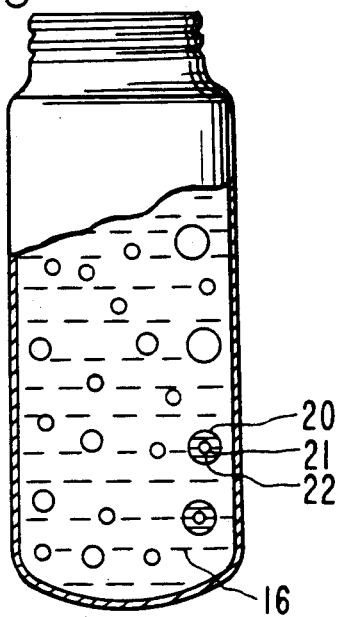
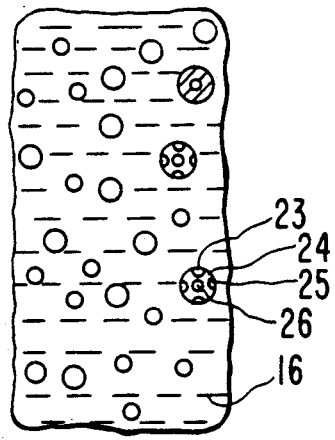
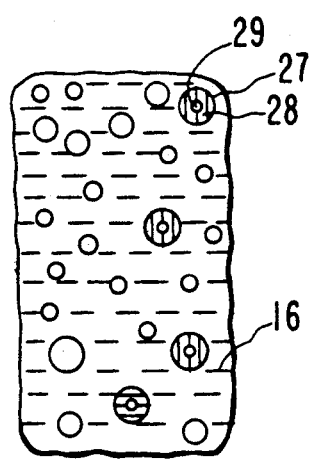
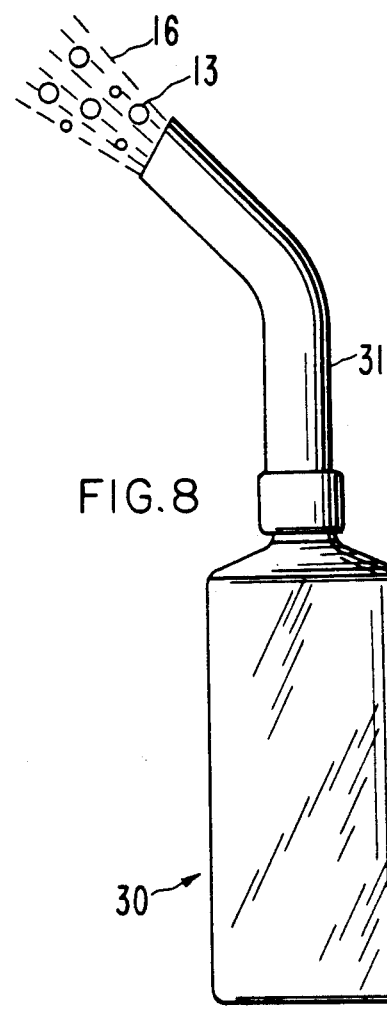

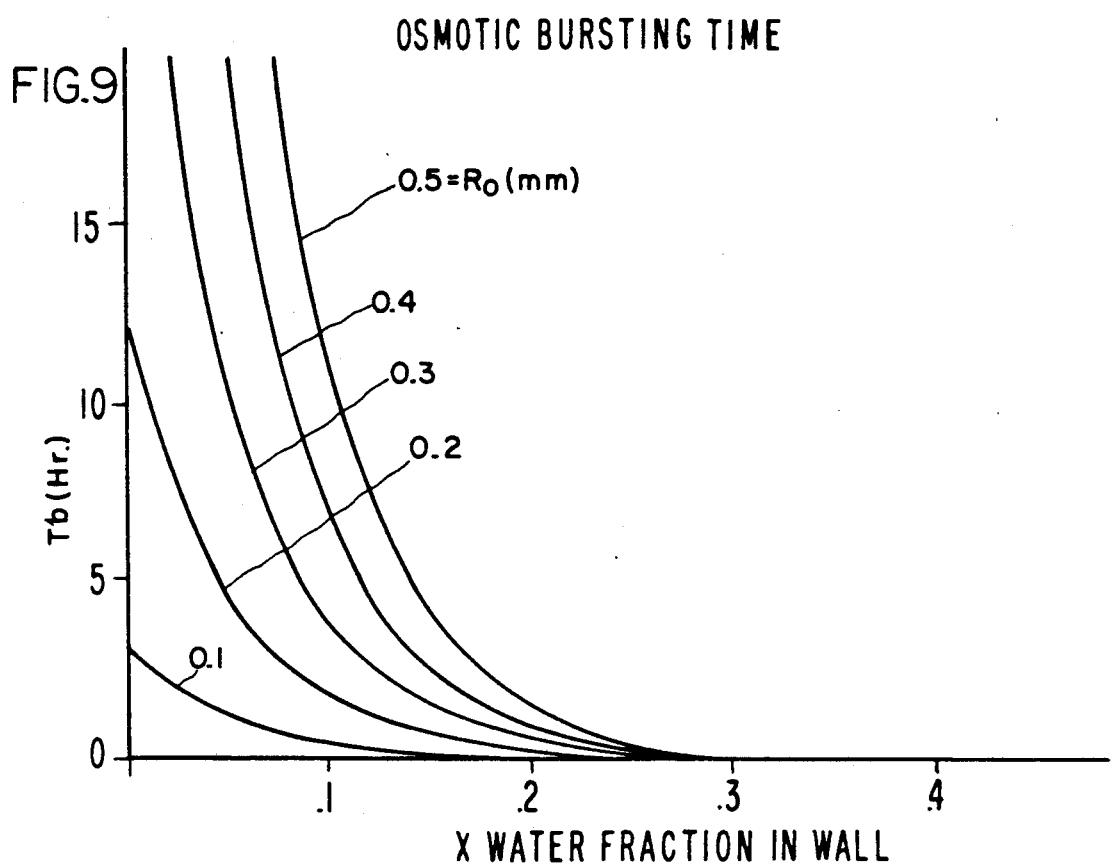
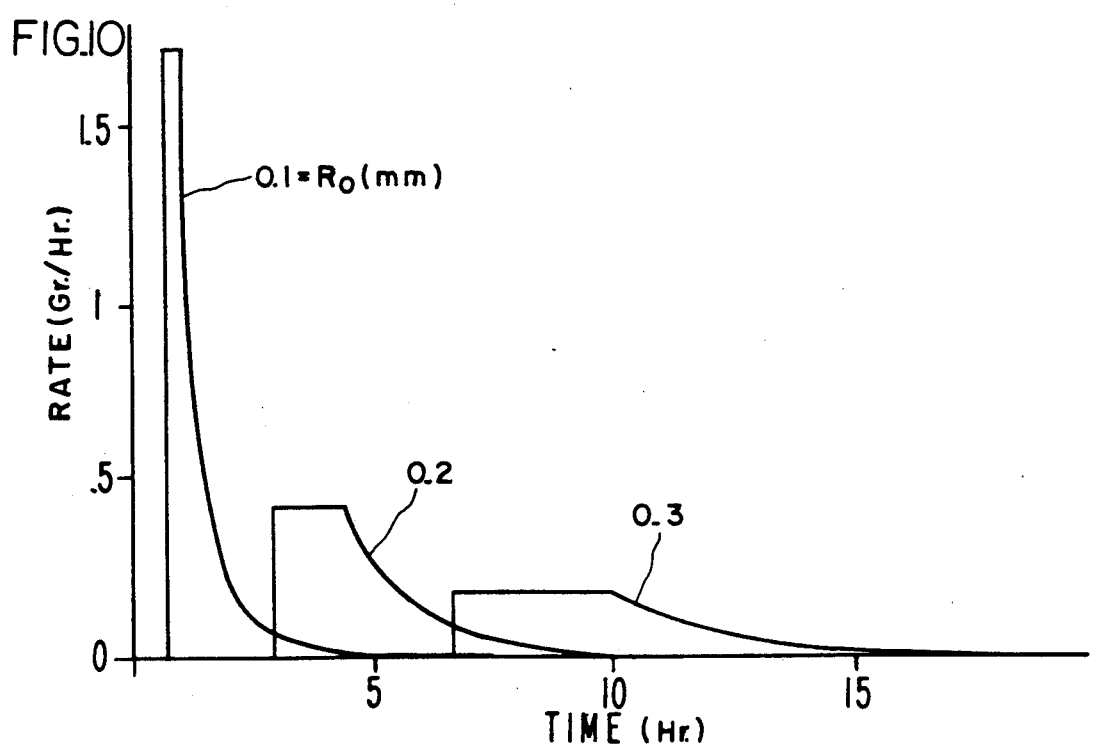

METHOD FOR DELIVERING DRUG IN TINY PILLS IN LIQUID CARRIER

CROSS-REFERENCE TO RELATED APPLICATIONS

This application is a continuation of U.S. patent application Ser. No. 07/112,189 filed Oct. 26, 1987, now U.S. Pat. No. 4,853,229 issued Aug. 1, 1989, which appln. is incorporated herein and benefit is claimed of its filing date. These applications are copending with U.S. patent application Ser. No. 07/337,197 filed April 12, 1989. These applications are assigned of record to ALZA Corporation of Palo Alto, Calif.

FIELD OF THE INVENTION

This invention pertains to a novel and useful drug delivery system. More particularly the invention concerns a drug delivery system comprising a plurality of tiny pills in a pharmaceutically acceptable liquid carrier.

BACKGROUND OF THE INVENTION

Tiny pills manufactured as small, round, solid dosage forms comprising a medicinal agent surrounded by a film are known to the medical and to the pharmaceutical arts. The tiny pills known to the prior art are delivered in a conventional manner to a host dispersed in a solid, dry carrier such as a compressed tablet comprising the tiny pills, or a polymeric matrix comprising the tiny pills. In another dosage form the prior art delivered the tiny pills housed in the dry lumen of a conventional capsule.

Tiny or small pills and dosage forms comprising tiny pills in a dry tablet, matrix or dry capsule for dispensing a medicinal agent are known in the following references: Lipowski, G.B. Pat. 523,594; Laboratorie de Rechersches, G.B. Pat. 1,098,006; Blythe, U.S. Pat. No. 2,738,003; Svedres, U.S. Pat. No. 2,793,979; Wagner, U.S. Pat. No. 2,897,121; Reese, U.S. Pat. No. 2,921,883; Swintosky, U.S. Pat. No. 2,951,792; Press, U.S. Pat. No. 2,953,497; Barry, U.S. Pat. No. 2,996,431; Sheppard, U.S. Pat. No. 3,080,294; Eng, U.S. Pat. No. 3,081,233; Sheppard, U.S. Pat. No. 3,109,775; Neville, U.S. Pat. No. 3,139,383; Gaunt, U.S. Pat. No. 3,328,256; Speiser, U.S. Pat. No. 3,390,050; Chester, U.S. Pat. No. 3,492,397; Raghunathan, U.S. Pat. No. 4,221,778; Urquhart and Theeuwes, U.S. Pat. No. 4,434,153; Urquhart and Theeuwes, U.S. Pat. No. 4,578,075; Urquhart and Theeuwes, U.S. Pat. No. 4,642,233; Urquhart and Theeuwes, U.S. Pat. No. 4,649,043 and Urquhart and Theeuwes, U.S. Pat. No. 4,659,558.

The above presentation teaches that delivery systems have been provided to deliver tiny pills. While those delivery systems provide for delivering the tiny pills, there are serious and inherent short-comings associated with these delivery systems. For example, tiny pills in a tablet may not be available for instant release to the environment of use. Tablets usually are made in a tabletting machine under an applied pressure of a ton or more and this compressive force absorbed by the tablet can seriously delay the release of the tiny pills. Tiny pills dispersed in a polymeric matrix may not be available because they are entrapped in the molecular structure of the polymer. Additionally, well known serious short-comings are associated with the administration of dry capsules containing tiny pills. Dry capsules are not a conducive means for administering a drug to a patient with a dry or sore throat, they are bulky and hard to swallow, and they do not lend themselves for administering a needed drug to children. It will be appreciated by those versed in the dispensing art, in view of the above presentation, that a critical need exists for a delivery system for making tiny pills available instantly and continuously to an environment of use. The need exists for providing tiny pills for (a) achieving an early therapeutically effective plasma concentration of drug and for (b) achieving a continuous and therapeutically effective plasma concentration of drug. A delivery system is needed for housing and for providing tiny pills for (c) dispersing the drug in a drug receiving environment for (d) increasing the bioavailability of the drug, (e) for concomitantly decreasing the likelyhood of local irritation of mucosal tissue, and (f) for masking the unpleasant taste of many drugs.

OBJECTS OF THE INVENTION

Accordingly, in view of the above presentation, it is an immediate object of this invention to provide both a novel and useful drug delivery system that makes a substantial contribution to the art by providing a delivery system useful for obtaining better therapy in the management of health and disease.

Another object of the present invention is to provide a delivery system for both housing and delivering tiny pills, and which delivery system overcomes the short-comings associated with the prior art.

Another object of the present invention is to provide a delivery system for making available tiny pills throughout the environment of use for improving the availability and the absorption of a drug and for minimizing local irritation of a biological drug receiving environment.

Another object of the invention is to provide a delivery system for administering tiny pills to the gastrointestinal tract with a delivery system that is relatively economical in cost to manufacture, provides the clinician in the hospital with a dependable delivery system, and is well-adapted for practical and acceptable use in the home.

Another object of the present invention is to provide a delivery system for administering a drug in the gastrointestinal tract by making available a delivery system comprising a multiplicity of miniature pills that spread and deliver drug over a large area of the gastrointestinal tract.

Another object of the present invention is to provide a delivery system comprising a multiplicity of orally administrable tiny pills that are simple in construction and exhibit all the practical benefits of controlled and continuous administration of drug in the stomach and in the intestine for executing a therapeutic program.

Another object of the present invention is to provide a delivery system comprising a plurality of tiny pills comprising a drug, which tiny pills are dispersed in a pharmaceutically acceptable liquid carrier that exhibits means for substantially preventing a premature delivery of drug from the tiny pills while the tiny pills are in the liquid carrier.

Another object of the invention is to provide a pharmaceutically acceptable carrier comprising a plurality of tiny pills wherein the release of drug is delayed from the tiny pills by governing the pH of the carrier for preventing the loss of integrity of the wall of the tiny pills.

Another object of the present invention is to provide a delivery system comprising a pharmaceutically acceptable liquid carrier housing a multiplicity of tiny pills wherein the liquid carrier suspends the tiny pills over time.

Another object of the present invention is to provide a delivery system comprising a plurality of tiny pills that can dispense at least two different drugs at a controlled rate for obtaining the pharmacological logical and physiological benefits of each drug, and which system thusly represents an improvement and an advancement in the delivery arts.

Another object of the present invention is to provide a delivery system housing tiny pills for dispensing two drugs essentially free of chemical interaction attributed to chemical incompatibility, thereby overcoming the problems associated with the prior art.

Another object of the invention is to provide a delivery system comprising tiny pills in a fluidic vehicle, and whereing the tiny pills exhibit prolonged storage and shelf life.

These objects as well as other objects, features and advantages of the invention will become more apparent from the following detailed description of the invention, the drawings and the accompanying claims.

BRIEF DESCRIPTION OF THE DRAWINGS

In the drawings, which are not drawn to scale but are set forth to illustrate various embodiments of the invention, the drawing figures as as follows:

FIG. 3 is similar to FIG. 2 wherein FIG. 3 illustrates tiny pills that release a beneficial drug by an osmotic process;

FIG. 5 is a view of a delivery system comprising tiny pills in a fluidic means which tiny pills deliver a beneficial drug by the process of diffusion;

FIG. 6 is a view of a delivery system comprising tiny pills in a fluid environment, which tiny pills release a beneficial drug through a microporous wall;

FIG. 7 is a view of a delivery system comprising tiny pills in a fluid environment, which tiny pills release a beneficial drug by a process of erosion;

FIG. 8 illustrates a container with a pouring member useful for storing and then pouring the delivery system to a spoon, or the like, for administering the delivery system to a patient;

FIG. 9 is a graph depicting the osmotic bursting time for delivery systems provided by the invention;

FIG. 10 is a graph depicting the rate of delivery of drug from osmotic bursting delivery systems;

In the drawings and specifications, like parts in related drawing figures are identified by like numbers. The terms appearing earlier in the specification and in the description of the drawings as well as embodiments thereof are further described elsewhere in the disclosure.

DETAILED DESCRIPTION OF THE DRAWINGS

Figure 1:
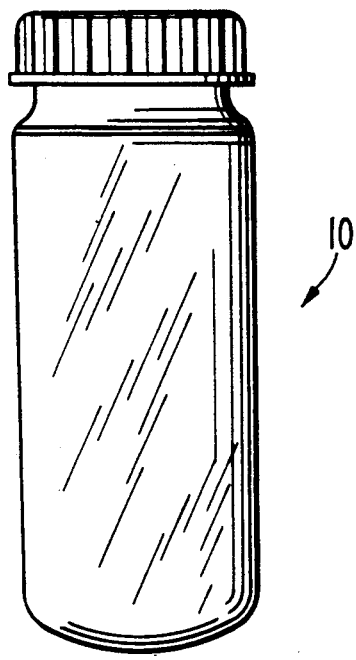
FIG. 1 depicts a container that can be used for containing the delivery systems provided by the invention.
Figure 2:
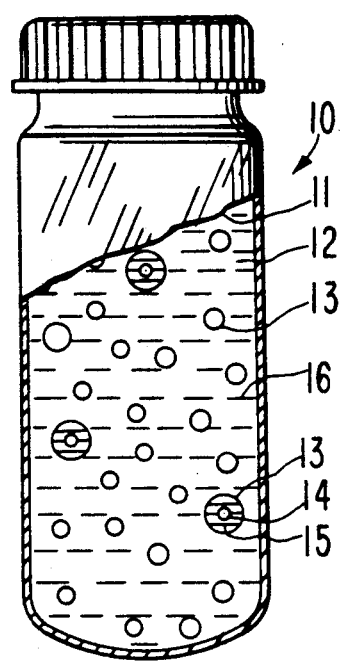
FIG. 2 is an opened view of a container for depicting a delivery system provided by the invention, which delivery system comprises tiny pills in a fluid medium.

Turning now to the drawings in detail, which are an example of the various delivery systems provided by the invention, and which example is not to be construed as limiting, one example of a delivery system is seen in FIGS. 1 and 2. In FIG. 1 a container 10 is illustrated for housing the delivery system provided by the invention. The container can be any receptacle for holding a liquid, and the like, such as a bottle made of glass or plastic, a capsule, cup, beaker, and the like.

In FIG. 2 container 10 of FIG. 1 is seen in opened-section at 11 for illustrating a lumen 12 that houses a delivery system provided by the invention. The delivery system comprises a multiplicity of tiny pills 13. Tiny pills 13 are a first dispensing means for the controlled delivery of a beneficial agent, such as a drug, both immediately and over a prolonged period of time. Tiny pills 13, an agent dispensing means, comprise a core of beneficial agent 14, such as a drug, surrounded by a wall 15 formed of a release rate controlling material. Tiny pills 13 can have a wall 15, in one embodiment, made from a composition that releases beneficial agent 14 in the stomach, or tiny pills 13 can have a wall 15, in another embodiment, made from an enteric composition which prevents release of beneficial agent 14 in the stomach, but will release beneficial agent 14 in the intestine. Additionally, the composition comprising wall 15 can be selected, in presently preferred embodiments, from wall-forming nontoxic compositions that release beneficial agent 14 by different physical-chemical mechanisms. These mechanisms include osmosis, diffusion, erosion, disintegration, metabolism, and like mechanisms. Wall 15 can have various thicknesses as an additional aid for providing immediate timed release and prolonged timed release of beneficial agent 14.

The delivery system provided by the invention comprises also means 16. Means 16, a pharmaceutically acceptable carrier, comprises a liquid and it is a second dispensing means for (a) containing tiny pills 13, (b) for delivering tiny pills 13 to an environment of use such as a drug receptor, (c) for governing the release of beneficial agent 14 from the tiny pills 13, and (d) for keeping the shelf life of the tiny pills. Means 16 comprises a nontoxic, inert fluidic carrier such as a member selected from the group consisting of an inorganic liquid, an organic liquid, aqueous media, emulsion, suspension, liquid comprising semisolids, elixir, syrup, juice, osmotic solution, viscous solution, hydrogel solution, gel suspension in a water media, pharmacologically acceptable liquid, semisolid comprising a liquid and a solid, and the like. Means 16, in a presently preferred embodiment, governs and substantially prevents a premature release of beneficial agent 14 from tiny pills 13 into a liquid means 16 in container 10. Means 16 governs the release of beneficial agent 14 by exhibiting an osmotic pressure or a concentration in a liquid means 16 that is substantially equal to, or higher than the osmotic pressure or the concentration gradient exhibited by beneficial agent 14 across wall 15 of tiny pills 13 against liquid means 16. For example, for a beneficial agent 14 exhibiting an osmotic pressure of $\pi_b$, or for a beneficial agent 14 blended with an osmotically effective solute exhibiting an osmotic pressure of $\pi_t$, the osmotic pressure exhibited by liquid means 16 is equal to $\pi_L$, or greater than $\pi_L$, such that $\pi_L \geq \pi_t$, where $\pi_t$ is the osmotic pressure of the tiny pills. This inventive feature provides also means for storing the delivery system essentially-free of drug release during storage.

The osmotic pressure or the concentration of liquid means 16 can be regulated by adding a composition of matter to liquid means 16. The composition of matter can be in any physical form such as powder, particle, crystal, strip, film, granules, fiber, and the like. The composition of matter additionally can comprise a beneficial agent, an osmagent or an osmopolymer. Osmagents are known also as osmotically effective compounds and as osmotically effective solutes. The beneficial agent can be a drug that is the same or different than a drug in a tiny pill. Representative osmagents useful for blending with the liquid include carboxylic acids such as dicarboxylic, tricarboxylic, hydroxydicarboxylic, hydroxytricarboxylic and dihydroxycarboxylic acids such as tartaric, citric, maleic, succinic, fumaric, mixtures thereof, and the like; examples of osmotically active solutes include solutes such as sodium chloride, magnesium sulfate, magnesium chloride, potassium chloride, sodium sulfate, lithium sulfate, potassium acid phosphate and the like; carbohydrates such as raffinose, succrose, glucose, lactose, galactose, altrose, monosaccharides, disaccharides, polysaccharides, mixtures thereof, and the like; examples of alcohols include alcohols such as sorbitol also known as hexanehexol, mannitol and the like; examples of gels include such as gum Arabic, agar, acacia, tragacanth, and the like; Other ingredients that can be added to the liquid include urea, inositol and like osmotic solutes.

The osmotic solute is present in any physical form that is compatible with a host, and with the tiny pills. The osmotic pressure of a solution of variously osmotically active compounds and a solution of a beneficial agent such as a drug used for making tiny pills is measured in a commercially available osmometer that measures the vapor pressure difference between pure water and the solution to be analyzed and, according to standard thermodynamic principles, the vapor pressure ratio is converted into an osmotic pressure difference. An osmometer that can be used for the present measurements is identified as Model 320B, Vapor Pressure Osmometer, manufactured by the Hewlett Packard Co., Avondale, Pa. Procedures for measuring osmotic pressure using thermodynamic principles are disclosed in U.S. Pat. Nos. 4,160,020 and 4,576,604.

Figure 3:
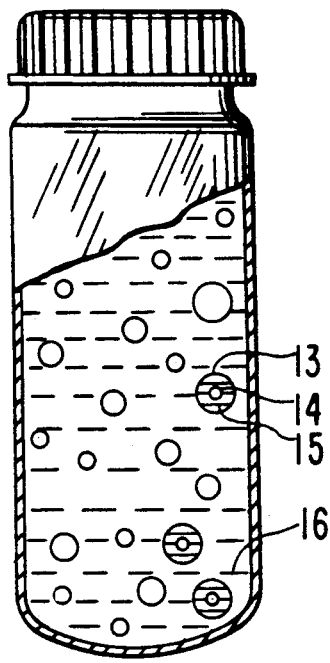

FIG. 3 is an opened section depicting a delivery system provided by the invention. FIG. 3 illustrates a plurality of tiny pills 13 that release a drug by osmotic principles. In FIG. 3, tiny pills 13 comprise a wall 15 that releases a beneficial agent 14 by the process of osmotic bursting over time. In a presently preferred embodiment, beneficial agent 14 is a drug. The drug, in one embodiment, is present in the form of an osmotic solute, such as a therapeutically acceptable salt, that exhibits an osmotic pressure gradient across wall 15 against distilled water, or the drug can be mixed with an osmotically effective solute that exhibits an osmotic pressure gradient across wall 15 against distilled water. In FIG. 3, in the embodiment illustrated, fluidic means 16 comprises a concentration substantially equal to or larger than the concentration of drug 14 in tiny pill 13 thereby providing an initial concentration gradient substantially equal to zero. The wall forming composition used to manufacture wall 15 comprises those materials permeable to the passage of an external fluid present in an environment of use and substantially impermeable to the passage of drug and osmotic solute. Typical materials include a member selected from the group consisting of cellulose acylate, cellulose diacylate, cellulose triacylate, cellulose acetate, cellulose diacetate, cellulose triacetate, cellulose acetate having a degree of substitution, D.S., up to 1 and an acetyl content of 21%; cellulose diacetate having a D.S. of 1 to 2 and an acetyl content of 21% to 35%; cellulose triacetate having a D.S. of 2 to 3 and an acetyl content of 35% to 44.8%; cellulose acetate propionate, cellulose acetate butyrate, ethyl cellulose semipermeable polyurethane, and the like. The osmotic wall can be coated around the drug in varying thicknesses by pan coating, spray-coating, Wurster ® fluid air-suspension coating, coacervation techniques, and the like. The wall is applied using organic solvents such as methylene chloride-methanol, methylene chloride-acetone, methanol-acetone, ethylene dichloride-acetone, and the like. Osmotic wall forming materials, and procedures for forming the wall, and osmotic bursting procedures are disclosed in U.S. Pat. Nos. 2,799,241; 3,952,741; 4,014,334 and 4,016,880.

Drug 14, neat, or a combination of drug 14 and osmotically effective solute in pill 13, in one embodiment, will have a particle size of 0.1 to 1000 micron, and a presently preferred particle size of about 0.5 to 300 microns, average. Procedures for measuring the surface area average diameter of agent solutes are reported in *J. Am. Chem. Soc.*, Vol. 6, p 309, (1938); *The Surface Chemistry of Solids*, by Gregg, 2nd Ed., (1961), published by Remhold Corp., N.Y.; in *Absorption, Surface Area and Porosity*, by Gregg et al., (1967), published by Academic Press, N.Y.; in *Physical Absorption of Gases*, by Yound et al., (1962), published by Butterworth and Co., Ltd., London; and in *Fine Particle Measurements*, by Valla, (1959), published by Macmillan Co., N.Y.

Procedures for ascertaining the impermeability or the permeability of a polymer film used for providing wall 15 of osmotic bursting pill 13 are known to the art in *Proc. Roy. Sci.*, London, Series A, Vol. 148, (1935); *J. Pharm. Sci.*, Vol. 55, pp 1224-29, (1966); in *Diffusion in Solids, Liquids and Gases*, by Jost, Chapter XI, pp 436-88, (1960), published by Academic Press, Inc., N.Y. Procedures for measure osmotic bursting aperture formation in a polymeric film by the hydrostatic pressure in the pill exceeding the cohesive integrity of the polymeric film, with the polymer wall 15, can be determined by measurements predicted on pressure-deflection and mechanical behavior measurement techniques reported in *Modern Plastics*, Vol. 41, pp 143-44, 146 and 186, (1964); *Handbook of Common Polymers*, by Scott et a., pp 588-609, (1971), published by CRC Press, Cleveland, Ohio; in *Machine Design*, pp 107-11, (1975); in *J. Sci. Instruments*, Vol. 42, pp 591-96, (1965); and by measuring mechanical stress-strain patterns of polymers using the Instron ® Testing Machine, available from the Instron Corporation of Canton, Mass.

Figure 4:
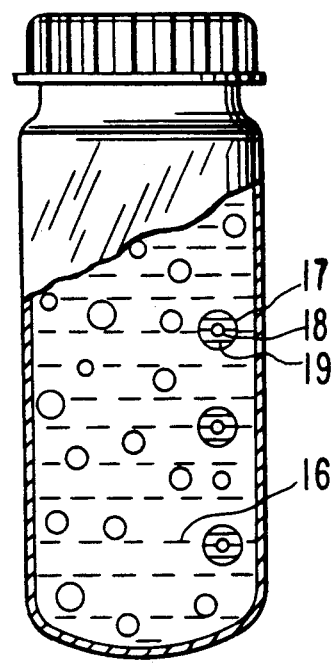
FIG. 4 is a view of a delivery system comprising tiny pills in a fluid which tiny pills release a drug by controlled disintegration.

In FIG. 4 another delivery system is seen provided by the invention. In FIG. 4 tiny pills 17 comprise drug 18 surrounded by wall 19 of tiny pill 17 initially present in fluidic means 16. Wall 19 in the illustrated embodiment comprises a composition consisting essentially of a fatty ester mixed with a wax. Representative fatty esters include a member selected from the group consisting of triglyceryl ester, glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glyceryl monodeconate, glyceryl didecenoate, and glyceryl tridecenoate.

The wax, in one representative embodiment, included in the wall forming composition is a member selected from the group consisting essentially of beeswax, cetyl palmitate, spermacetic wax, carnauba wax, cetyl myristate, cetyl cerotate, stearyl palmitate, stearyl myristate, and lauryl laurate.

The tiny pills provided by the invention, in presently preferred optional embodiments, can comprise an enteric coat. The enteric coat can be in contact with the outer surface of the wall comprising the tiny pill, or the wall can be made of an enteric composition. The enteric coat is made from an enteric materials that do not dissolve or disintegrate in the stomach during the period of time the tiny pill passes through the stomach. The enteric materials suitable for forming enteric coat or wall include: (a) enteric materials that are digestible by enzymes in the small intestine; (b) enteric materials containing an ionizable polyacid; (c) enteric materials that are a long-chain polymer with an ionizable carboxyl group, and the like.

Representative enteric materials include: (d) a member selected from the group of phthalates consisting essentially of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxpropl methylcellulose hexahydrophthalate, polyvinyl acetate phthalate, and the like., (e) a member selected from the group consisting of keratin, keratin sandarac-tolu, salol, salol beta-napthyl benzoate and acetotannin, salol with balsam of Peru, salol with tolu, salol with gum mastic, salol and stearic acid, and salol and shellac; (f) a member selected from the group consisting of formalized protein, formalized gelatin, and formalized cross-linked gelatin and exchange resins; (g) a member selected from the group consisting of myristic acid-hydrogenated castor oil-cholesterol, stearic acid-mutton tallow, stearic acid-balsam of tolu, and stearic acid-castor oil; (h) a member selected form the group consisting of shellac, ammoniated shellac, ammoniated shellac-salol, shellac-wool fat, shellac-acetyl alcohol, shellac-stearic acid-balsam of tolu, and shellac-n-butyl stearatel (i) a member selected from the group consisting of abietic acid, methyl abietate, benzoin, balsam of tolu, sandarac, mastic with tolu, and mastic with acetyl alcohol; (j) a member selected form the group consisting of cellulose acetate with shellac, starch acetate phthalate, polyvinyl acid phthalate, 2-ethoxy-5-(2-hydroxyethoxymethyl)-cellulose phthalic acid, acid phthalates of carbohydrates, zein, alkyl resin-unsaturated fatty acids-shellac, colophony, mixtures of zein and carboxymethylcellulose, and the like. The enteric materials are discussed in *Remington's Pharmaceutical Sciences*, 13th Ed., pp 604–05, (1965), published by Mack Publishing Co., Easton, Pa.

The composition comprising the ester and the wax can be coated around the drug by using an organic solvent such as a member selected from the group consisting of carbon tetrachloride, chloroform, trichloroethylene, ether, benzene, ethyl acetate, methyl ethyl ketone, isopropyl alcohol, and the like. Tiny pills 17 are dispersed in a carrier means 16 in which the tiny pills keep their integrity, such as hypertonic emulsion. The fatty esters, waxes, solvents and procedures for making tiny pills that slowly disintegrate in a gastrointestinal tract in a period of 8 to 12 hours are disclosed in U.S. Pat. No. 2,793,979. The tiny pills also can be stored in a liquid carrier wherein the pH is adjusted to maintain the integrity of the tiny pills during storage. For example, the tiny pills are stored in a low or high pH liquid means wherein the wall and the coat stay intact, and when orally administered the wall or the coat contact the acid pH of the stomach or the basic pH of the small intestine to release the contents of the pills in the respective biological environment.

FIG. 5 depicts another delivery system provided by the invention. In FIG. 5 the delivery system comprises tiny pills 20, comprising wall 22 that surrounds drug 21. Wall 22 is made of a drug release rate controlling material. That is, drug 21 dissolves in wall 22 and passes through wall 22 at a controlled rate over time. Tiny pills 20 are stored in liquid means 16. The liquid means can comprise a pH or a media in which the drug is salted out of solution in the wall at the liquid wall interface to delay diffusion of the drug through the wall. On administration, the biological environment allows the drug to diffuse through the wall for its intended therapeutic effect.

Exemplary materials for forming drug release rate controlling diffusional wall comprise ethylene vinyl acetate copolymer, polyethylene, cross-linked polyvinylpyrrolidone, vinylidene chloride-acrylonitrile copolymer, polypropylene, silicone, and the like. The wall can be applied by the techniques described above and materials suitable for forming wall 22 are described in U.S. Pat. Nos. 3,938,515; 3,948,262 and 4,014,335.

The rate of release of drug 21 through wall 22 can be determined easily by standard procedures. In this manner particularly materials used as the wall as the drug release rate controlling barrier for release of drug from the tiny pills can be selected. Various techniques, such as the transmission method, the sorption/desorption method, and the like, can be used as measurers of permeability. One technique that has been found to be eminently well suited is to cast or hot press a film of the material to a thickness in the rate of 1 to 60 mils. The film is used as a barrier between a rapidly stirred (e.g., 150 rpm) saturated solution of the drug and a rapidly stirred solvent bath, both maintained at constant temperature (typically 37° C.). Samples are periodically withdrawn from the solvent bath and analyzed for drug concentration. By plotting the agent's concentration in the solvent bath, versus time, the permeability constant P of the material is determined by the Fick's First Law of Diffusion.

Slope of plot $= (Q_2 - Q_1)/(t_2 - t_1) = p\ AC/h$, wherein $Q_1 =$ cumulative amount of drug in receptor solvent at $t_1$ $Q_2 =$ cumulative amount of drug in receptor solvent at $t_2$ $t_1$ = elapsed time to first sample, i.e., $Q_1$
$t_2$ = elapsed time to second sample, i.e., $Q_2$
A = area of membrane in cm$^2$
C = initial concentration of drug
h = thickness of membrane in cm By determining the scope of the plot, i.e., $(Q_2-Q_1)/(t_2-t_1)$ and solving the equation using the known or measured values of A, C, and h, the permeability P constant in cm$^2$/time of the material for a given drug is readily determined.

The release rate through different drug release controlling materials can be easily ascertained by standard techniques known to the art as recorded in *J. Pharm. Sci.*, Vol. 52, pp 1,145 to 1,149; and *ibid.*, Vol. 53, pp 798–802, (1964); *ibid.*, Vol. 54, pp 1,459 to 1,464, (1965); *ibid.*, Vol. 55, pp 840–43 and 1,224 to 1,239, (1966); *Encyl. Polymer Sci. Technol.*, Vols. 5 and 9, pp 65–82 and 794–807, (1968); the references cited therein, in U.S. Pat. Nos. 3,845,480; 3,845,761 and 3,896,819.

FIG. 6 depicts another delivery system provided by the invention. In FIG. 6 the delivery system comprises tiny pills 23 comprising wall 24 containing a pore forming agent 25, which wall surrounds a core of drug 26. Tiny pills 23 are dispersed in liquid means 16. Wall 24 can be a wall forming material selected from the group consisting of microporous olefin polymer, vinyl polymer, styrene polymer, acrylate polymer, acrylonitrile polymer, vinylidene polymer, amide polymer, ester polymer, phenolic polymer, aldehyde polymer, rubber polymer, organosilicon polymer, and the like. The polymer composition additionally contains a pore former that is leached from wall 24 when the delivery system is in an environment of use. Representative pore formers comprise a member selected from the group consisting of alkali metal salts, alkali earth metal salts, monosaccharides, disaccharides, polysaccharides, polyalcohols and the like. In one presently preferred embodiment the pore formers comprise the polyalcohols such as mannitol and sorbitol. In operation, in a gastrointestinal tract, pore former 25 leaves wall 24 thereby providing an exit port for drug 26 to be administered to the gastrointestinal tract. The delayed release of drug 26 is effected by adding solubility modifiers to liquid 16, by buffering liquid 16 to delay the leaching of a pore former 25, or by adjusting the pH of the liquid to a pH in which a pore former is poorly or practically insoluble.

FIG. 7 illustrates another embodiment provided by the invention. In this embodiment tiny pills 27 comprise an erodible wall 28 that surrounds a core 29 of drug formulation. Wall 28 is made in a preferred embodiment of a bioerodible polymeric composition that bioerodes at a controlled and continuous rate in an environment of use. Bioerodible materials useful for forming wall 28 include bioerodible polyvalent acid or alkali mobile cross-linked polyelectrolyte, bioerodible polycarboxylic acid, bioerodible polyester, bioerodible polyamide, bioerodible polyimide, bioerodible polylactic acid, bioerodible polyglycolic acid, bioerodible polyorthoester, and bioerodible polycarbonates. The polymers used for manufacturing the wall are selected in one embodiment based on the polymer's action in an acidic or basic liquid member. For example, if hydrogen ions, or hydroxyl ions start the erosion of the erodible polymer, the liquid is made with an opposite ionic nature. A liquid member can be provided that corresponds to the liquid composition of the gastrointestinal tract and, for example, if the polymer is acid labile the liquid member comprises a neutral or a basic pH. The invention thus provides an added embodiment for delaying the release of drug from a tiny pill by governing the pH of means 16. The polymers and procedures for forming wall 28 are disclosed in U.S. Pat. Nos. 3,811,444; 3,867,519; 3,888,975; 3,971,367; 3,993,057 and 4,138,344. The erosion kinetics of erodible polymers are known in *Controlled Release of Bioactive Materials*, edited by Baker, pp 1–17, published in 1980 by Academic Press: *CRC Critical Reviews in Therapeutic Drug Carrier Systems*, edited by Heller, Vol. 1, pp 39–90, (1984); *Erodible Controlled Release Systems*, edited by Baker and Lonsdale, pp 235–242, published by ACS, (1976); *Controlled Release From Eridible Slabs, Cylinders and Spheres*, by Hopfenberg, pp 229–234, published by ACS, (1976); *Blok. J. Int. Biodetn. Bull.*, 11, pp 78–84, (1975); and in *Recent Advances in Drug Delivery Systems*, edited by Heller, pp 101–21, (1984), published by Plenum Press, N.Y.

In the specification and in the accompanying claims the term, "beneficial agent" includes drug. The term, "drug" includes pharmacologically active substances that produce a local or systemic effect in animals, which term includes warm-blooded mammals such as humans. The active drug that can be delivered includes drugs that act on the central nervous system, depressants, hypnotics, sedatives, psychic energizers, tranquilizers, anticonvulsants, muscle relaxants, anti-Parkinson agents, analgesics, anti-inflammatories, hormonal agents, anti-histamines, contraceptives, sympathomimetics, nasal decongestants, diuretics, anti-parasites, neoplastics, hypoglycemics, opthalmics, electrolytes, cardiovascular drugs, and the like.

Exemplary drugs that are soluble in water and can be delivered by the devices of this invention include prochlorperazine edisylate, ferrous sulfate, aminocaproic acid, potassium chloride, mecamylamine hydrochloride, procianamide hydrochloride, amphetamine sulfate, benzhetamine hydrochloride, isoproternol sulfate, methamphetamine hydrochloride, phenmetrazine hydrochloride, bethanechol chloride, methacholine chloride, atropine sulfate, methascopolamine bromide, isopropamide iodide, tridihexethyl chloride, oxprenolol hydrochloride, methoprolol hydrochloride, cimetidine hydrochloride, dextromethorphan, and the like.

Exemplary drugs that have limited solubility in water and can be delivered by devices of this invention include meclizine hydrochloride, phenoxybenzamine, thiethylperazine maleate, anisindone, erythrityl titranitrate, dizoxin, reserpine, acetazolamide, methazolamide, bendroflumethiazide, chlorpropamide, tolazamide, chlormadinone acetate, aluminum aspirin, methotrexate, acetyl sulfisoxazole, erytbhromycin, progestins, estrogine, progestational, corticosteroids, and the like.

Examples of other drugs that can be delivered by the devices include aspirin, indomethacin, naproxen, fenoprofen, sulidac, diclofenac, indoprofen, propanolol, metroprolol, oxprenolol, timolol, clonidine, theophylline, ferrous lactate, phenoxybenzamine, baclofen, furosemide, and the like. The beneficial drugs are known in the art in *Pharmaceutical Sciences*, by Remington, 14th Ed., 1979, published by Mack Publishing Co.; *The Drug, The Nurse, The Patient, Including Current Drug Handbook*, by Falconer et al., (1974–1976), published by Saunder Company; and *Medicinal Chemistry*, 3rd Ed., Vols. 1 and 2, by Burger, published by Wiley-Interscience Co.

The drug can be present in the tiny pill in various forms, such as unchanged molecules, molecular complexes, therapeutically acceptable salts such as hydrochlorides, hydrobromides, sulfates, oleates, and the like. For acid drugs, salts of metals, amines, or organic cations, quaternary ammonium salts can be used. Derivatives of drugs such as esters, ethers and amides can be used. Also, a drug that is water insoluble can be used in a form that is the water soluble derivative thereof to serve as a solute and, on its release from the device, is converted by enzymes, hydrolyzed by body pH or other metabolic process to the original biologically active form.

The amount of drug present in a tiny timed pill generally is from about 10 ng to 50 mg. The number of tiny pills in a given amount of liquid means is from 10 to 1000 in, for example, a ml of liquid, or more. The tiny pills comprising an exterior wall and an inner core of drug generally have a diameter of about 50 microns to a diameter of 4000 microns and in a presently preferred embodiment a diameter of at least 200 microns. The wall thickness can vary as an aid in controlling the release of drug, with wall thickness exemplified as from 0.01 mm to 3.00 mm and the like.

The following examples are merely illustrative of the present invention, and they should not be considered as limiting the scope of the invention in any way, as these examples and equivalents thereof will become apparent to those versed in the delivery art in light of the present disclosure and the accompanying claims.

EXAMPLE 1

An orally administrable dosage form comprising tiny pills of a cough suppressant housed in a liquid member is prepared as follows: first, dextromethorphan hydrobromide and succinic acid in a ratio of 0.5 to 1 are blended and blended with hydroxypropylmethylcellulose in bead form, and then divided in three equal fractions of three different sizes of 0.1, 0.2 and 0.3 mm radius. The spherical beads are coated next with a wall forming composition. The composition comprises a blend of cellulose acetate having an acetyl content of 39.8% and cellulose acetate butyrate comprising an acetyl content of 29% and a butyryl content of 17%. The cellulose acetate and the cellulose acetate butyrate are present in a 50:50 blend, the cellulose acetate butyrate has a permeability k equal to $2 \times 10^{-5}$ cm·mil/hr, and the cellulose acetate has a permeability k or $10^{-4}$ cm·mil/hr. The wall forming composition is applied from an organic solution containing methylene chloride and to the wall applied in a ratio of 1 to 1. Next, the solvent is stripped from the pills and the tiny pills permitted to dry at room temperature. Then the tiny pills are added to a liquid means comprising 5 ml of lemon tincture, 5 ml of orange tincture, 0.5 gm sodium saccharide, 65 ml propylene glycol, 15 ml glycerin and sorbitol solution to 100 ml. The dosage form optionally can be stored in Container 30, as seen in FIG. 8. Container 30 is equipped with a pouring member 31 for delivering tiny pills 13 in liquid means 16 to a spoon, or the like, for administering to a patient.

EXAMPLE 2

Another dosage form is prepared by following the procedure of Example 1, except that in this example dextromethorphan and mannitol are blended as dry particles in a ratio of 10 to 1. The particles are coated in a fluid air suspension machine with a composition of ethyl cellulose in ethanol to surround the drug core with a wall of the cellulose to yield tiny pills thereof. After the solvent is vacuum stripped from the tiny pills, the pills are blended with a solution comprising sorbitol, propylene glycol, alcohol, water and orange oil.

EXAMPLE 3

Another dosage form is provided by coating a drug core composition comprising phenylpropanolamine hydrochloride, lactose and magnesium stearate in a fluid air suspension machine with a composition comprising ethyl cellulose in ethanol to surround the drug core with a wall of ethyl cellulose to yield tiny pills thereof. After the solvent is vacuum stripped from the tiny pills, the pills are blended with a solution comprising sorbitol, propylene glycol, alcohol, water and orange oil.

EXAMPLE 4

The above manufacture can be repeated by replacing the ethyl cellulose and ethanol with cellulose acetate having an acetyl content of 39% in methylene chloride-methanol wall-forming solvent; or by applying a bioerodible wall of poly(2,2-dioxo-trans-1,4-cyclohexane dimethylene tetrahydrofuran) around the drug core. The latter bioerodible polymer is applied by heating the polymer to 80°-90° C. and then coating the drug cores. The tiny pills in both manufacture are added to a hypertonic liquid means.

EXAMPLE 5

A dosage form is manufactured by first preparing sustained release tiny pills by blending 40 g of polyvinyl pyrrolidone with 375 g of theophylline, the blend kneaded and passed through an extrusion granulation machine to produce drug cores with an average radius of 0.1 mm. After drying at 115°-120°, the drug cores are coated with a wall of ethyl cellulose in an air suspension machine to yield tiny pills. The tiny pills are added to a liquid means comprising 0.8 g of powdered gelatin type A, 50 ml of edible oil and sufficient water to 100 ml. The liquid means is prepared by following the procedure in *Pharmaceutical Sciences*, by Remington, 14th ed., (1970), p 1492, published by Mack Publishing Co., Easton, Pa. The dosage form can be used for orally administering the bronchodilator for the management of status asthmaticus and as a pulmonary vasodilator and smooth muscle relaxant. Other forms of theophylline can be used in the subject dosage form such as theophylline sodium acetate, theophylline sodium glycinate, [7-(2,3-dihydroxypropyl)] theophylline, theophylline meglumine, and theophylline monoethanolamine.

EXAMPLE 6

In another manufacture, the dosage form is made by first preparing sustained tiny pills by blending 400 ml of ethyl cellulose-water, 70:30 solution, 7.5% w:v, with 375 g of theophylline, 150 g of mannitol and 475 g of magnesium stearate and the blend kneaded and passed through an extrusion granulation machine. After drying at 115°-120° F., the core are passed through a 20 mesh screen and coated with a wall of ethyl cellulose in an air suspension machine to yield tiny pills. The tiny pills are added to a liquid means comprising 0.8 g of powdered gelatin type A, 0.8 g of tartaric acid, 0.1 g of citric acid, 0.1 g of ascorbic acid, 6 ml of alcohol, 50 ml of edible oil and sufficient water to 100 ml. The liquid means is prepared by following the procedure in *Pharmaceutical Sciences*, by Remington, 14th Ed., (1970) p 1492, published by Mack Publishing Co., Easton, Pa. The dosage form can be used for orally administering the bronchodilator for the management of status asthmaticus and as a pulmonary vasodilator and smooth muscle relaxant. Other forms of theophylline can be used in the subject dosage form such as theophylline sodium acetate, theophylline sodium glycinate, [7-(2,3-dihydroxypropyl)] theophylline, theophylline meglumine, and theophylline monoethanolamine.

EXAMPLE 7

Other delivery systems comprising tiny pills are made by spraying non-pareil cores with an edible adhesive and then dusting the adhesive coated core with a drug. The drug coated core then is coated with an appropriate edible enteric coat to provide enteric coated tiny pills. In a preferred manufacture at least one enteric coat is applied in this embodiment of the invention, but more than one coat, usually 1 to 20 separate coats, can be used for the present purpose. Manufacturing procedures for tiny pills are taught in U.S. Pat. No. 3,365,365.

EXAMPLE 8

In another embodiment the tiny pills can be made from a core of carbohydrate, such as sucrose, dusted with a mixture of talc, starch and galactose, moistened with distilled or deionized water, and the desired medicinal such as the antibiotic erythromycin. The pills are dried and then coated with an outer layer of a nontoxic, enteric wall former selected from the group consisting of keratin, calcium alginate, shellac, partially hydrolyzed styrene-maleic acid copolymer polyvinylacetate phthalate, polyvinyl hydrogenphthalate, and the like. Finally, the tiny pills are dispersed and/or suspended in an acidic liquid means adapted for oral admittance into the gastrointestinal tract. Procedures for manufacturing the tiny pills are described in U.S. Pat. No. 3,081,233.

EXAMPLE 9

A drug with an osmotic pressure of 100 atmospheres, atm, as ascertained by using an osmometer, is granulated into particles of various size radius from 0.1 to 0.5 mm. A wall forming polymer is coated in a ratio of 1:1 onto the drug. The elongation defined as the ratio of the increase in radius at bursting to the original radius of the particle is 0.5. The polymer selected for the coating process can have a variety of water sorption characteristics resulting in a water content of up to 30 percent, or $X=0.3$. The bursting time by osmosis for each tiny pill is given in accompanying FIG. 9. In FIG. 9, Tb(Hr) is the bursting time in hours for a tiny pill, $R_o$ is the radius in mm of the uncoated particle, and X is the fraction of water in the wall. From FIG. 9, it is clear that a total mass of formulation can be prepared with various mass fractions of particle sizes which are coated with various polymers of different elongation and water sorption.

EXAMPLE 10

A drug delivery system is prepared comprising tiny pills in a liquid means. The tiny pills deliver the drug by osmotic bursting of the wall to form in the gastrointestinal environment a drug release orifice in the wall of the tiny pill. The tiny pills were prepared from osmotic particles of drug exhibiting an osmotic pressure of 40 atm, and the drug was shaped into spheres of 0.1, 0.2 and 0.3 mm. The liquid means has an equivalent or higher osmotic pressure. The polymer comprising the wall had an elongation of 0.5 mm and a water permeability of $25 \times 10^{-8}$ cm$^2$/hr. The drug has a density of 1.2 g/ml. One gram of the drug exhibited a bursting time and a delivery rate dependent of the radius of the particle as shown in accompanying FIG. 10. In FIG. 10, $R_o$(mm) is the radius of the particles in mm, and Rate (gr/hr) is the rate of drug delivery in grams per hour. The study indicates, from the accompanying FIG. 10, that a mixture of particles can be provided to give a release rate given by Equation (a) wherein $f_1$, $f_2$, $f_3$ are in Equation (a) the fraction of particles present of rate $R_1$, $R_2$ and $R_3$, respectively.

$$R = f_1 R_1 + f_2 R_2 + f_3 R_3 \quad (a)$$

The drug dextromethorphan hydrobromide exhibits an osmotic pressure of 40 atm. The osmotic solute sucrose in aqueous solution is formulated to an osmotic pressure exceeding 40 atm.

EXAMPLE 11

The delivery of a drug from a tiny pill that releases the drug by osmotic bursting of the wall to provide a drug releasing orifice is seen from the following presentation and the accompanying equations. The tiny osmotic bursting pills in an aqueous media that is hypotonic compared to the compositon inside the tiny pills imbibes water into the tiny pills. In the absence of a preformed orifice in the wall of the tiny pill, the imbibed aqueous fluid causes the tiny pill to swell and a volume increase occurs during which time period ($\Delta t_1$) the delivery rate from the system is low. When the internal hydrostatic pressure exceeds the pressure necessary to rupture the wall, the release rate increases to a maximum during the period $\Delta t_2$, after which the rate again decreases when all the solid excess drug from the core is delivered. A typical curve depicted in FIG. 11.

The release rate from the osmotic bursting tiny pills is described by Equation (1) with $(dV/dt)_t$ given by Equation (2).

$$\frac{dm}{dt} = \left(\frac{dV}{dt}\right)_t \cdot C + \left(\frac{dm}{dt}\right)_D \quad (1)$$

$$\left(\frac{dV}{dt}\right)_t = \frac{A}{h} \cdot L_P (\sigma \Delta \pi - \Delta P) - \left(\frac{dV}{dt}\right)_V \quad (2)$$

wherein in Equation (1) and Equation (2), C is the concentration of the drug solution hydrodynamically pumped, $(dm/dt)_D$ is the amount of drug delivered by diffusion through the wall, $(dV/dt)_t$ is the total volume of solution hydrodynamically pumped from the tiny pill which is equal to the volume of water imbibed by the tiny pill as set forth in Equation (3), minus the volume increase of the tiny pill per unit time $(dV/dt)_V$.

$$\left(\frac{dV}{dt}\right)_i = \frac{A}{h} L_P (\sigma \Delta \pi - \Delta P) \quad (3)$$

Further, wherein A is the wall area, h is the wall thickness, $\sigma$ the reflection coefficient of the wall, $\Delta \pi$ and $\Delta P$ are the osmotic and hydrostatic pressure difference between the inside and outside of the wall From the time, $t=0$, a small amount of drug is usually delivered in the absence of an orifice by diffusion through the wall as described by $(dm/dt)_D$. During this time period, $\Delta t_1$, the volume increase is equal to the volume imbibed, as set forth in Equation (3a).

$$\left(\frac{dV}{dt}\right)_i = \left(\frac{dV}{dt}\right)_V \text{ and therefore } \left(\frac{dV}{dt}\right)_t = 0 \tag{3a}$$

Figure 11:
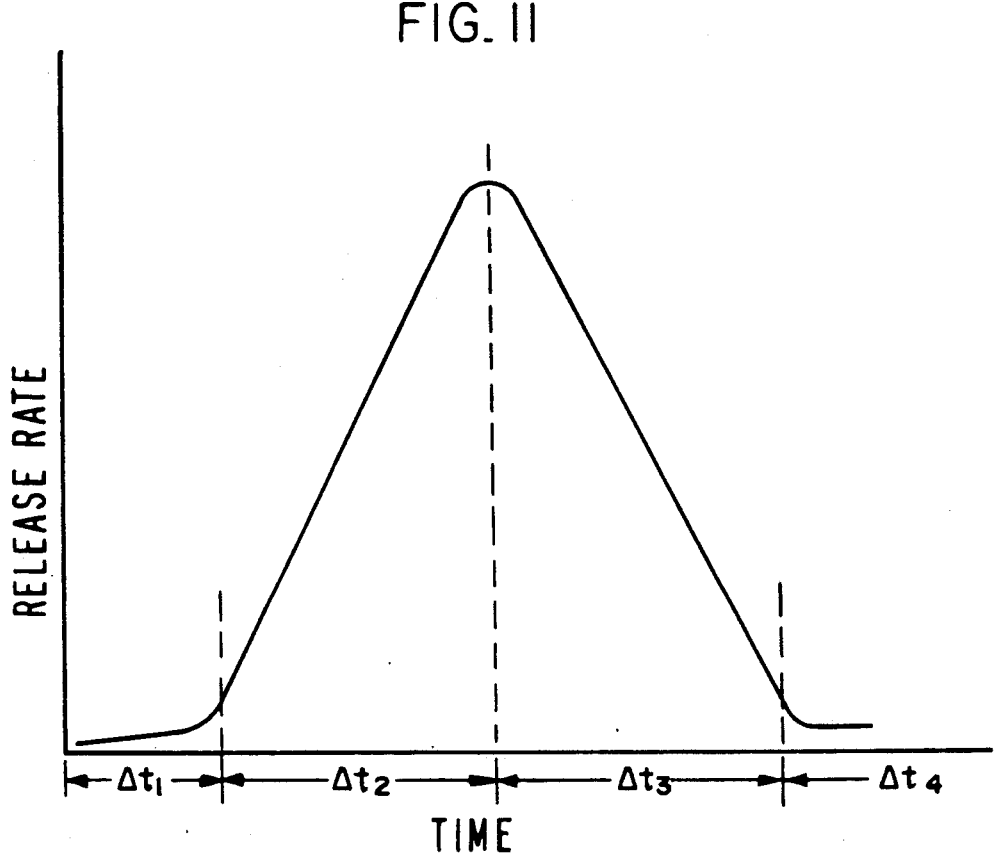
FIG. 11 depicts the rate of release from an osmotic bursting aperture forming delivery system.
Figure 12:
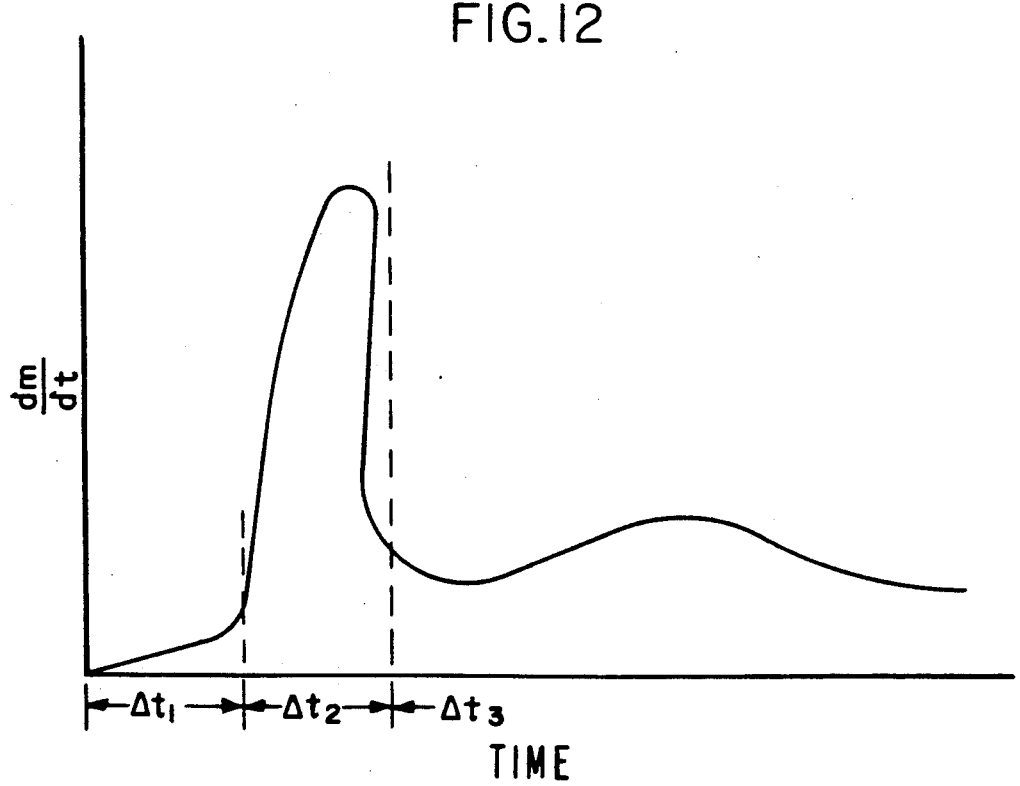
FIG. 12 depicts the effects of deformation on a wall of a delivery system.
Figure 13:
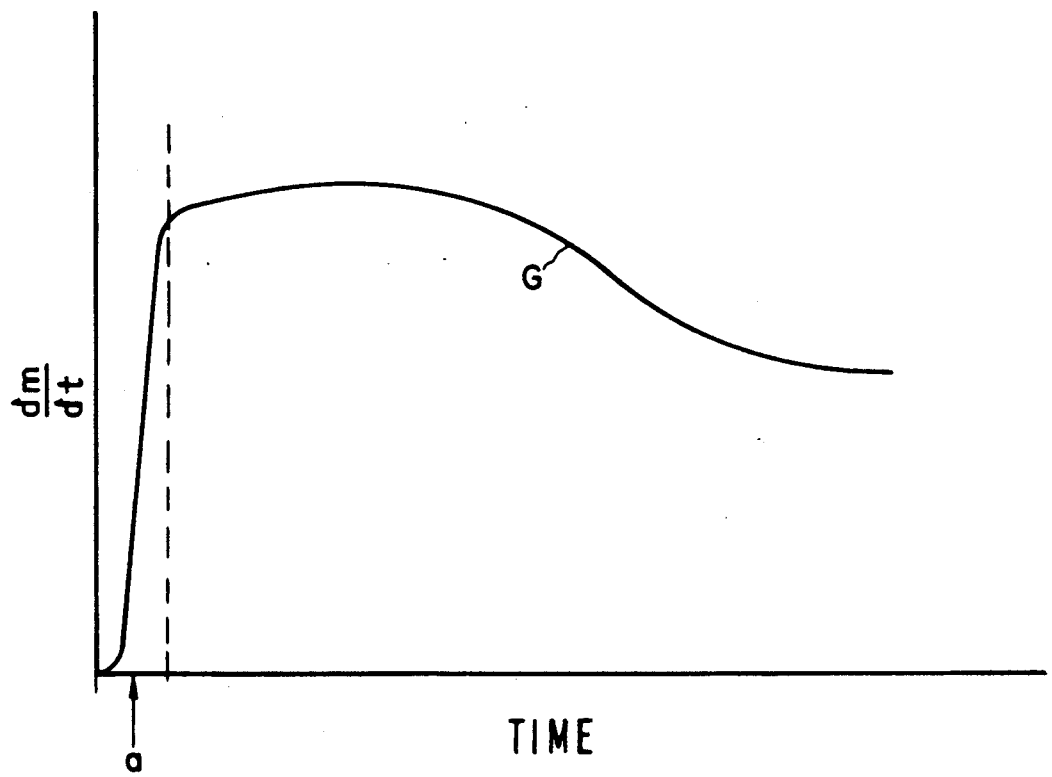
FIG. 13 depicts the zero order rate of release from a delivery system over time; and, FIG. 14 is an opened view for illustrating the structure of a delivery system.

The effect of the volume stretching during the period $\Delta t_1$ is twofold: 1. delay in delivery and 2. the system potential zero order delivery profile is substantially shortened since the amount of drug that is delivered at a non-zero order rate is seen in Equation (4):

$$M_{NZ_O} = S \cdot V \tag{4}$$

wherein V is the volume at the time of bursting, which is larger than the undeformed volume. S is drug solubility. According to Equation (5) the mass not delivered at zero order is:

$$M_{NZ} = S\left[V_0 + \left(\frac{dV}{dt}\right)_i \cdot \Delta t_1\right] \tag{5}$$

since the volume deformation associated with FIG. 11 is largely plastic or permanent deformation. Thus, by selecting the mechanical properties of the wall and thereby controlling the function $(dV/dt)_V$, as a function of pressure or elongation, several release rate profiles can be programmed for the tiny pills as described by the basic spike type curve obtained by plastic deformation of the wall as seen in FIG. 11, and by selecting an elastic wall a curve can be obtained as seen in FIG. 12. In FIG. 12, $\Delta t$ is the elastic deformation, $\Delta t_2$ is the elastic recovery and $\Delta t_3$ is the osmotic pump kinetics. Thus, by selecting a brittle wall wherein early aperture formation occurs without deformation, a zero order rate profile can be obtained for the tiny pills, as seen in FIG. 13, wherein a is the brittle fracture and b is the release rate for a conventional zero order curve.

Figure 14:
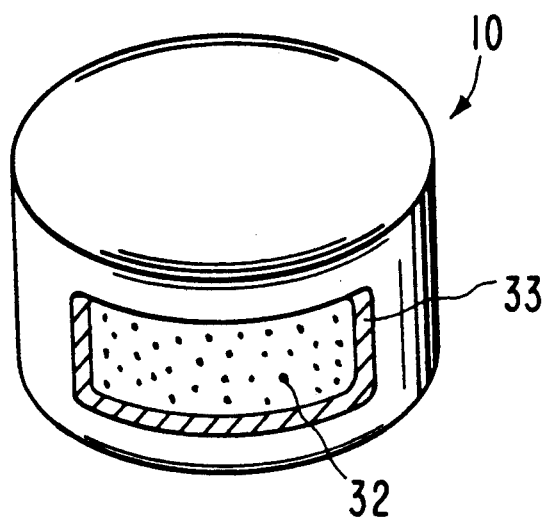

Accompanying FIG. 14 illustrates in opened section a tiny pill designed for releasing a drug by an osmotic bursting mechanism. In FIG. 14, a pill is seen comprising an osmotically active drug core 32 surrounded by a semipermeable wall 33. In operation, when pill 10 is in a water environment, it imbibes water by osmosis and the internal volume increase per unit time is described by Equation (6):

$$\frac{dV}{dt} = k \cdot \frac{A}{h} (\Delta \pi - \Delta P) \tag{6}$$

wherein A is the area of the semipermeable wall, h is the thickness of the wall, k is the permeation constant, $\Delta \pi$ is the osmotic pressure difference between the solution inside and outside the tiny pill, and $\Delta P$ is the hydrostatic pressure differences between the inside and the outside of the pill.

The internal volume expands from $V_o$, the volume at time zero, to $V_b$, the volume at bursting time, $t_b$. The bursting time is obtained from Equation (6) and given by Equation (7):

$$t_b = \int_{V_o}^{V_b} \frac{h \cdot dV}{k \cdot A(\Delta \pi - \Delta P)} \tag{7}$$

The quantities h, k, A, $\pi$, and P are all functions of volume; and during the initial stages of swelling when the solution inside the system is saturated, Equation (8) holds:

$$\Delta \pi = \pi^o \tag{8}$$

and when the osmotic pressure of the outside solution is negligible, $\pi^o$ is the osmotic pressure inside the system up to a volume V, as expressed by Equation (9):

$$V = \frac{M_p}{S} \tag{9}$$

wherein $M_p$ is the mass of the drug particle and S is the solubility of the drug. Thus, for most applications, the volume at bursting $V_b$ is smaller than V as given by Equation (8) and Equation (9). The quantities A, h, and V can conveniently be expressed as a function of the system radius r as seen in Equation (10) and Equation (11):

$$A = 4\pi r^2 \tag{10}$$

$$V = \frac{4}{3} \pi r^3 \tag{11}$$

Assuming that the drug wall deforms at constant volume results in Equation (12):

$$h = \left(\frac{r_o}{r}\right)^2 h_o \tag{12}$$

For a thin walled system, the mass of the wall is given by Equation (13):

$$M_c = 4\pi r_o^2 \cdot h_o \cdot \rho_c \tag{13}$$

wherein $\rho_c$ is the density of the wall. The mass of the drug is given by Equation (14):

$$M_p = \frac{4}{3} \pi r_o^3 \cdot \rho_p \tag{14}$$

wherein $\rho_p$ is the density of the drug. The ratio of drug to the wall weight from Equation (13) and Equation (14) is combined in Equation (15):

$$\frac{M_p}{M_c} = \frac{r_o \cdot \rho_p}{3 \cdot h_o \cdot \rho_c} \tag{15}$$

accompanied by the assumption $\rho_p \cong \rho_c$, then Equation (16) follows:

$$\frac{M_p}{M_c} = \frac{r_o}{3 h_o} \tag{16}$$

Thus, for a soft walled system wherein the hydrostatic pressure P can be neglected compared to the osmotic pressure, Equation (7) can be simplified to Equation (17) by substituting Equation (12) as follows:

$$t_b = r_o^2 \cdot \frac{h_o}{k} \int_{r_o}^{r_b} \frac{dr}{r^2 \cdot \pi_o} \tag{17}$$

Equation (17) results in Equation (18) and Equation (20) by substituting Equation (19) and Equation (16) as follows:

$$t_b = \frac{r_o \cdot h_o}{\pi_o \cdot k}\left(1 - \frac{r_o}{r_b}\right) \tag{18}$$

$$\frac{r_b - r_o}{r_o} = El \tag{19}$$

$$t_b = \frac{r_o^2}{3 \cdot \pi_o \cdot k} \cdot \frac{M_c}{M_p} \cdot \frac{El}{1 + El} \tag{20}$$

The zero order delivery rate from the capsule pill system follows the osmotic bursting of each wall of the pill system wherein delivery of drug by osmosis is given by Equation (21):

$$\frac{dm}{dt} = k \cdot \pi_o \cdot \frac{A}{h} \cdot S \tag{21}$$

for a total mass of drug $M_{to}$ containing N particles of mass $M_o$ the total surface area is $A_{to}$ such that Equation (22) and Equation (23) result in Equation (24) set forth as follows:

$$A_{to} = N \cdot 4\pi r_o^2 \tag{22}$$

$$M_{to} = N \cdot \frac{4}{3}\pi r_o^3 \cdot \rho_p \tag{23}$$

$$A_{to} = \frac{3 \cdot M_{to}}{r_o \cdot \rho_p} \tag{24}$$

The delivery rate given by Equation (21) contains the ratio A/h of area and a wall thickness at the time of bursting. This ratio can be calculated as a function of the original value $A_o/h_o$ and the elongation El. According to Equation (12) it follows that Equation (25) results.

$$\frac{A}{h} = \frac{A_o \cdot h_o}{h^2} \tag{25}$$

substituting Equation (12) in Equation (25) yields Equation (26).

$$\frac{A}{h} = \frac{A_o \cdot h_o^4}{r_o^4 \cdot h_o^2} = \frac{A_o}{h_o}\left(\frac{r}{r_o}\right)^4 \tag{26}$$

$$r = (El + 1) r_o \tag{27}$$

Equation (27) exists according to Equation (19) such that Equation (26) and Equation (27) result in Equation (28):

$$\frac{A}{h} = \frac{A_o}{h_o}(El + 1)^4 \tag{28}$$

The total release rate of N particles of drug follows from Equation (21) and Equation (28) to yield Equation (29) as follows:

$$\frac{dm_t}{dt} = k \cdot \pi_o \cdot S \cdot N \cdot \frac{A_o}{h_o}(El + 1)^4 \tag{29}$$

Since $N \cdot A_o$ is given by Equation (24), Equation (30) results as follows:

$$\frac{dm_t}{dt} = K \cdot \pi_o \cdot S \cdot \frac{3 M_{to}}{r_o \cdot h_o \cdot \rho_p}(El + 1)^4 \tag{30}$$

The drug loading is defined by Equation (31):

$$L = \frac{M_p}{M_c} \tag{31}$$

followed by substituting Equation (16) in Equation (30) results in Equation (32) as follows:

$$\frac{dm_t}{dt} = k \cdot \pi_o \cdot S \cdot M_{to} \cdot (El + 1)^4 \cdot \frac{9 \cdot L}{r_o^2 \cdot \rho_p} \tag{32}$$

and for a single particle system, Equation (33) and Equation (34) are presented as follows:

$$\frac{dm}{dt} = k \cdot \pi_o \cdot S \cdot M_p \cdot (El + 1)^4 \cdot \frac{9 \cdot L}{r_o^2 \cdot \rho_p} \tag{33}$$

$$\frac{dm}{dt} = 37.7 \times k \pi_o \cdot S \cdot r_o \cdot L (1 + El)^4 \tag{34}$$

Control over the bursting time and release rate can then be programmed by selecting drug and osmotic properties, respectively $\pi_o$ and S, loading L, drug particle size, $r_o$, and the wall composition which defines k, and El for the above described system with a wall from which delivery occurs in the extended state at $r = r_b$, the release rate and bursting time are inversely proportional as can be seen by eliminating $r_o^2$ between Equation (33) and Equation (20) as shown in Equation (35):

$$\frac{dm}{dt} = 3 \cdot \frac{S}{\rho_p} \cdot \frac{M_p}{t_b} \cdot El (1 + El)^3 \tag{35}$$

The duration of the zero order rate over $t_z$ of such a particle is given by Equation (36) where Z is the zero order rate:

$$t_z = \frac{M_{pz}}{Z} \tag{36}$$

wherein $M_{pz}$ is the mass delivered at zero order rate given by Equation (37).

$$\frac{M_{pz}}{M_p} = 1 - \frac{S}{\rho_p}\left(\frac{r}{r_o}\right)^3 \tag{37}$$

which is the same relation for an elementary osmotic pump for which $r = r_o$. The ratio of $r/r_o$ from Equation (19) yields Equation (38):

$$t_z = \frac{M_p\left[1 - \frac{S(1 + El)}{\rho_p}\right]}{Z} \tag{38}$$

From Equation (38) and Equation (33) it follows that:

$$t_z = \frac{r_o^2 [\rho_p - S(1 + El)]}{9 \cdot L \cdot k \pi_o \cdot S (1 + El)^4} \quad (39)$$

Thus, for mathematically ascertaining the time course from the initial burst to the end of the zero order delivery period, it now is possible to calculate the ratio of $t_z$ to $t_b$ from Equation (39) and Equation (20), the resulting Equation (40):

$$\frac{t_z}{t_b} = \frac{1}{3}\left[\frac{\rho_p}{S} - (1 + El)\right]\frac{1}{(1 + El)^3 \cdot El} \quad (40)$$

wherein Equation (40) holds for the delivery system except for the conditions $El=0$ when $t_b=0$.

The non-zero order rate of release from the tiny pill systems can be expressed by the equations presented below. Thus, according to this study, beyond the zero order time $t_z$ the bursted pills deliver in a manner like an elementary osmotic pump; however, at an extended volume consistent with the burst radius. This non zero order rate can be described in the usual probability declining manner where Z is the zero order rate according to Equation (41) as follows:

$$\frac{dm}{dt} = \frac{Z}{\left[1 + \frac{Z}{SV}(t - t_z)\right]^2} \quad (41)$$

Combining Equation (11) and Equation (19) leads to Equation (42):

$$\frac{dm}{dt} = \frac{Z}{\left[1 + \frac{Z}{S} \cdot \frac{0.24(t - t_z)}{r_o^3(1 + El)^3}\right]^2} \quad (42)$$

From Equation (20), Equation (39), Equation (34) and Equation (40) it is evident that the delivery profile of such particles is strongly dependent on the elongation El. For small values of $El \approx 0.5$, the zero order time is a small fraction of the bursting time $t_z/t_b = 0.3$ for an average drug with a particle density 1 g/ml and drug solubility 0.3 g/ml.

Thus, each individual pill will mostly have a small amount of its drug delivered at zero order. The design of a pill formulation will, by choice, be composed of a mixture of drug with different membrane compositions to adjust k and the bursting time. In addition to coating loading L and osmotic pressure of the drug formulation as well as pill size are very useful variables to control for several of the weight fractions of the formulation.

The wall permeability k is a function of the water sorption X defined by the fraction of water in the saturated wall. This function is described by Equation (43) to describe the data $X=0.02$ to $X=0.5$ as follows:

$$k = 3.5 \times 10^{-8} \exp(19.7 X) \quad (43)$$

k is in units [cm$^2$hr·atm]

From Equation (20) and Equation (43) the aperture bursting time in a tiny pill system up to 24 hours is in the approximate range of elongations of 0.1 to 0.5, a drug loading $L=0.1$ to 3, osmotic pressures up to 300 atm, the preferred drug particle size is $r_o=0.001$ to 0.1 cm, with wall permeabilities up to $9 \times 10^{-5}$ cm$^2$/hr·atm. The expressions also indicate that longer bursting times can be achieved for polymers with higher elongations.

EXAMPLE 12

A beneficial drug is administered to an animal host, such as a human at a controlled rate according to the method of administration provided by the invention. The method comprises the steps of: (A) admitting orally into the gastrointestinal tract of a human a delivery system comprising: (1) drug dispensing means comprising: (a) a core of a beneficial drug; and (2) wall means for controlling the release of the beneficial drug from the dispensing means, which wall means surrounds the core of beneficial drug; and (2) means for delaying the release of the beneficial drug from the drug dispensing means, said means a liquid composition comprising a plurality of the drug dispensing means; and (B) delivering the beneficial drug by permitting the environment of the gastrointestinal tract to contact and dilute the liquid composition, whereby the drug dispensing means release the beneficial drug at a controlled rate to the gastrointestinal tract over a prolonged period of time.

EXAMPLE 13

Another dosage form is provided by coating a drug core composition comprising procainamide hydrochloride, lactose and magnesium stearate in a fluid air suspension machine with a composition comprising ethyl cellulose in ethanol to surround the drug core with a wall of ethyl cellulose to yield tiny pills thereof. After the solvent is vacuum stripped from the tiny pills, the pills are blended with a solution comprising sorbitol, propylene glycol, alcohol, water and organe oil.

It will be appreciated by those versed in the art the present invention makes available novel and useful delivery system for dispensing a beneficial drug over a prolonged period of time. Also, it will be understood by those knowledged in the dispensing art that many embodiments of this invention can be made without departing from the spirit and scope of the invention, and the invention is not to be construed as limited, as it embraces all equivalents therein.

I claim:

1. A method for delivering a beneficial drug to the gastrointestinal fluid of an animal, wherein the method comprises:
   (a) admitting into the gastrointestinal fluid of the animal a delivery system, which system comprises:
      (1) a pharmaceutically acceptable carrier, said carrier comprising a member selected from the group consisting of an inorganic liquid, an organic liquid, an aqueous media, emulsion, suspension, liquid comprising semisolid, elixir, syrup, juice, osmotic solution, viscous suspension, hydrogel solution, gel solution in a water media, and semisolid comprising a liquid, which pharmaceutically acceptable carrier comprises:
      (2) a plurality of tiny pills comprising a 50 micron to 4000 micron diameter;
      (3) about 10 ng to 50 mg of a beneficial drug in the tiny pills; and,
      (4) a wall that surrounds the beneficial drug; said wall being a polymer and containing a pore former, said polymer being selected from the group consisting of olefin, vinyl polymers, styrene polymers, acrylate polymers, acrylonitrile polymers, vinylidene polymers, rubber polymers, organosilicone polymers and bioerodable polymers;

(b) diluting the pharmaceutically acceptable carrier with gastrointestinal fluid, thereby;
(c) delivering the beneficial drug by the tiny pills releasing the drug into the gastrointestinal fluid of the animal.

* * * * *